US009138412B2

(12) United States Patent
Reddy et al.

(10) Patent No.: US 9,138,412 B2
(45) Date of Patent: Sep. 22, 2015

(54) BIOEQUIVALENT FORMULATION OF EFAVIRENZ

(75) Inventors: Bandi Parthasaradhi Reddy, Andhra Pradesh (IN); Podili Khadgapathi, Andhra Pradesh (IN); Goli Kamalakar Reddy, Andhra Pradesh (IN)

(73) Assignee: HETERO RESEARCH FOUNDATION (IN)

( * ) Notice: Subject to any disclaimer, the term of this patent is extended or adjusted under 35 U.S.C. 154(b) by 1 day.

(21) Appl. No.: 13/505,002

(22) PCT Filed: Nov. 4, 2009

(86) PCT No.: PCT/IN2009/000625

§ 371 (c)(1), (2), (4) Date: May 16, 2012

(87) PCT Pub. No.: WO2011/055375

PCT Pub. Date: May 12, 2011

(65) Prior Publication Data

US 2012/0225121 A1 Sep. 6, 2012

(51) Int. Cl.

*A61K 45/06* (2006.01)
*A61K 9/00* (2006.01)
*A61K 9/14* (2006.01)
*A61K 9/16* (2006.01)
*A61K 9/28* (2006.01)
*A61K 31/536* (2006.01)

(52) U.S. Cl.

CPC ............ *A61K 9/1688* (2013.01); *A61K 9/2866* (2013.01); *A61K 31/536* (2013.01); *A61K 45/06* (2013.01); *A61K 2300/00* (2013.01)

(58) Field of Classification Search

CPC .......................... A61K 2300/00; A61K 45/06
USPC ................................................ 424/400, 489
See application file for complete search history.

(56) References Cited

U.S. PATENT DOCUMENTS

2002/0076436 A1* 6/2002 Batra et al. .................... 424/465

FOREIGN PATENT DOCUMENTS

| | | | |
|---|---|---|---|
| EP | 1332757 | A1 | 8/2003 |
| EP | 2172193 | A1 | 4/2010 |
| WO | 2006018853 | A2 | 2/2006 |
| WO | 2009026257 | A2 | 2/2009 |

OTHER PUBLICATIONS

Fitzpatrick. The FitzMill Theory. Jan. 25, 2008. FitzMill. pp. 1 and 3.*

International Search Report and Written Opinion; International Appliction PCT/IN2009/000625; International Filing Date Nov. 4, 2009; Date of Mailing Jul. 29, 2010; 8 pages.

Newman et al.; "Solid-state Analysis of the Active Pharmaceutical Ingredient in Drug Products"; DDT; 8(19); pp. 898-905; (2003).

"III. Effects of Particle Size Reduction"; in Polymorphism in Pharmaceutical Solids; Harry G. Brittain, Ed.; Marcel Dekker, Inc.; pp. 334-341; (1999).

* cited by examiner

*Primary Examiner* — Frederick Krass
*Assistant Examiner* — Tracy Liu
(74) *Attorney, Agent, or Firm* — Cantor Colburn LLP

(57) ABSTRACT

The present invention provides a suitable technique namely wet milling and the process for reducing the particle size of efavirenz and making a tablet or capsule formulation with desired bioavailability equivalent to the reference listed drug without loosing its characteristics.

9 Claims, No Drawings

BIOEQUIVALENT FORMULATION OF EFAVIRENZ

CROSS-REFERENCE TO RELATED APPLICATIONS

This application is a 371 of PCT/IN2009/000625 filed Nov. 4, 2009, under the provisions of 35 U.S.C. 119 and the International Convention for the protection of Industrial Property, which is incorporated herein by reference.

FIELD OF THE INVENTION

The present invention relates to a suitable technique and its process for the reduction of particle size of crystalline efavirenz form H1 and making an oral dosage form viz. tablets or capsules alone or in combination with one or more other active ingredients such as emitricitabine or tenofovir disoproxil fumarate. The pharmaceutical formulation according to the invention is bioequivalent to the reference listed drug (RLD) when bioavailability studies are conducted in humans.

BACKGROUND OF THE INVENTION

Efavirenz is a non-nucleoside reverse transcriptase inhibitor (NNRTI) and is used as part of highly active antiretroviral therapy (HAART) for the treatment of a human immunodeficiency virus (HIV) type 1.

Efavirenz is chemically, (4S)-6-chloro-4-(2-cyclopropylethynyl)-4-(trifluoromethyl)-2, 4-dihydro-1H-3, 1-benzoxazin-2-one also used in combination with other antiretroviral agents as part of an expanded post exposure prophylaxis regimen to reduce the risk of HIV infection in people exposed to a significant risk.

WO Patent Application Publication No. WO 2006/018853 discloses the synthesis of crystalline and amorphous form of efavirenz i.e. crystalline efavirenz form H1 and is characterized by an x-ray powder diffraction spectrum having peaks expressed as 29 at about 5.4, 10.4, 11.6, 12.5, 15.3, 20.1, 20.8, 22.5, 23.1, 25.7, 27.9, 28.5, 28.8, 29.5, 30.2 and 38.2 degrees.

As the form is new, the characteristics as well as its behavior in vivo are not known. Tablets were made using the conventional methods and conducted bioequivalence study and found that it is not bioequivalent to the RLD.

It is known that the degree of solubility can influence the bioavailability, attempts were made to increase the solubility using various techniques known in the prior art such as ultrasonication, particle coating and particle size reduction.

Ultrasonication was not successful in enhancing the solubility and retaining the characteristics of new polymorph of efavirenz.

Particle coating showed an improvement in retaining the characteristics of new polymorph but no change was observed in terms of solubility.

With the earlier expertise in developing the formulation of efavirenz, it has been found that there is a requirement of special particle size to increase the solubility in order to achieve the desired bioavailability and to make a formulation bioequivalent to the reference listed drug.

Different techniques were evaluated to reduce the particle size of efavirenz such as impact milling, fluid energy milling, wet milling and tumbling by ball mill.

Impact milling, fluid energy milling and tumbling by ball mill were failed to retain the characteristics of novel form. When the wet milling process developed by the inventor was applied to achieve particle size reduction, it has been found that there is no conversion of one form to another form of efavirenz.

The polymorph used in the process of size reduction by the process of invention is preferably efavirenz form H1.

Tablets and capsules were made with the obtained efavirenz after wet milling using pharmaceutically acceptable excipients like super disintegrant viz. crospovidone and sodium starch glycolate, diluent/filler viz. microcrystalline cellulose and lactose, glidant viz. talc, colloidal silicon dioxide, sodium benzoate and magnesium oxide, lubricant viz. magnesium stearate, zinc stearate, calcium stearate, sodium lauryl sulfate and sodium stearyl fumarate.

The tablets and capsules were submitted to bioequivalence study and found that these are bioequivalent with reference listed drug.

DETAILED DESCRIPTION OF THE INVENTION

According to one aspect of the present invention there is provided a suitable technique namely wet milling for obtaining the 90 volume-percent of the particles ($D_{90}$) in the range of 2 to 100 μm of crystalline efavirenz form H1 using high speed homogenizer with an aqueous dispersion of 1 to 15% W/V at a speed of 10000 to 30000 rpm.

Optionally, the aqueous dispersion further includes the solvents selected from isopropanol, methanol and acetone or a mixture there of.

Preferably, the concentration of the aqueous dispersion is 1.5 to 10% W/V, more preferably the aqueous dispersion is 5 to 8% W/V and still more preferably the aqueous dispersion is 2 to 3% W/V.

Preferably, the wet milling process is carried out at a speed of 12000 to 28000 rpm and more preferably at a speed of 15000 to 25000 rpm.

Preferably, the 90 volume-percent of the particles ($D_{90}$) in the range of 3 to 50 μm and more preferable in the range of 5 to 15 μm.

The term "μm" refers to "micrometer" which is $1\times10^{-6}$ meter.

No change in polymorph has been observed during the size reduction by the process of the invention.

According to another aspect of the present invention, there is provided a stable, bioequivalent tablet or capsule comprises efavirenz form H1 having a 90 volume-percent of the particles ($D_{90}$) in the range of 2 to 100 μm.

Preferably, the dosage form is in the form of tablet.

The pharmaceutical composition of compressed tablet or a capsule of the invention may contain one or more additional excipients. These excipients selected from diluents, disintegrants, surfactants, lubricants and glidants.

The preferable diluent is selected from microcrystalline cellulose and lactose.

Preferably, the disintegrant is selected from crospovidone and sodium starch glycolate. More preferably the disintegrant is crospovidone in the concentration of about 5.0 to 10.0% by weight relative to the total weight of the compressed tablet or capsule.

It is preferred that the surfactant is selected from sodium lauryl sulfate, docusate sodium, benzekonium chloride, benzethonium chloride and cetrimide. More preferable surfactant is sodium lauryl sulfate.

Glidant is selected from talc, colloidal silicon dioxide, sodium benzoate and magnesium oxide, preferably the glidant is silicon dioxide and/or sodium benzoate.

The preferable lubricant is selected from magnesium stearate, zinc stearate, calcium stearate, sodium lauryl sulfate and sodium stearyl fumarate. More preferable lubricant is magnesium stearate.

According to another aspect of the present invention, there is provided a tablet or capsule formulation of efavirenz form H1 is in an amount of 200 mg to about 600 mg in a single dosage unit, characterized in that the 90 volume-percent of the particles ($D_{90}$) of efavirenz form H1 used is in the range of 2 to 100 μm.

According to another aspect of the present invention, there is provided a tablet or capsule formulation of efavirenz form H1 characterized in that the 90 volume-percent of the particles ($D_{90}$) of efavirenz form H1 used is in the range of 2 to 100 μm in combination with emitricitabine or tenofovir disoproxil fumarate or both.

According to another aspect of the present invention, there is provided a process for preparing a tablet or capsule of efavirenz form H1, which comprises:

a. wet granulating of efavirenz form H1 with one or more pharmaceutically acceptable excipients;
b. drying the granules obtained in step (a) at 25 to 45° C.; and
c. compressing the dried granules into a tablet or filled in a capsule, characterized in that the process does not involve milling.

Preferably, the efavirenz form H1 is in the form of a tablet along with one or more pharmaceutically acceptable excipients.

The tablet formulation is optionally film coated.

Preferably, the drying may be carried out at 30 to 40° C.

EXAMPLES

Example 1

Wet Milling of 2.0% Dispersion of Efavirenz (Form-H1)

2 gm of efavirenz (form-H1) was accurately weighed and dispersed in 100 gm of water with laboratory stirrer. The above said dispersion was allowed to size reduction by homogenizer at 15000 rpm. After homogenization, the dispersion was filtered using nylon filter under vacuum and dried.

Example 2

Wet Milling of 2.0% Dispersion of Efavirenz (Form-H1)

2 gm of efavirenz (form-I) was accurately weighed and dispersed in 100 gm of water with laboratory stirrer. The above said dispersion was allowed to size reduction by homogenizer at 20000 rpm. After homogenization, the dispersion was filtered using nylon filter under vacuum and dried.

Example 3

Wet Milling of 2.0% Dispersion of Efavirenz (Form-H1)

2 gm of efavirenz (form-H1) was accurately weighed and dispersed in 100 gm of water with laboratory stirrer. The above said dispersion was allowed to size reduction by homogenizer at 25000 rpm. After homogenization, the dispersion was filtered using nylon filter under vacuum and dried.

Example 4

Wet Milling of 5.0% Dispersion of Efavirenz (Form-H1)

5 gm of efavirenz (form-H1) was accurately weighed and dispersed in 100 gm of water with laboratory stirrer. The above said dispersion was allowed to size reduction by homogenizer at 30000 rpm. After homogenization, the dispersion was filtered using nylon filter under vacuum and dried.

Example 5

600 mg Tablet Formulation

| S. No | Ingredients | Mg/tab | % w/w |
|---|---|---|---|
| 1 | Efavirenz (form-H1) | 600.0 | 44.44 |
| 2 | Microcrystalline cellulose | 170.0 | 12.59 |
| 3 | Sodium lauryl sulfate | 35.0 | 2.59 |
| 4 | Cross Carmellose Sodium | 94.5 | 7.00 |
| 5 | Lactose monohydrate | 400.0 | 29.63 |
| 6 | Colloidal silicon dioxide | 33.5 | 2.48 |
| 7 | Magnesium stearate | 17.0 | 1.26 |
| Core Weight | | 1350 | |
| Coating weight buildup | | 27 | |
| Total tablet weight | | 1377 | |
| Coating material Composition | | | |
| 1 | Hypromellose | | |
| 2 | Polyethylene Glycol | | |
| 3 | Yellow Iron Oxide | | |
| 4 | Titanium Dioxide | | |

Method of manufacture: Efavirenz (form-H1) is mixed with other ingredients and then wet granulated using an aqueous solution of sodium lauryl sulfate. This wet mass may then be dried in a fluid bed, tray or other suitable dryer. The dried granules are blended and lubricated. This blend is compressed into tablets. The compressed tablets are film coated.

Example 6

600 mg Tablet Formulation

| S. No | Ingredients | Mg/tab | % w/w |
|---|---|---|---|
| 1 | Efavirenz (form-H1, $D_{90}$ = 100 microns) | 600.0 | 44.44 |
| 2 | Microcrystalline cellulose | 200.00 | 14.81 |
| 3 | Sodium lauryl sulfate | 46.00 | 3.41 |
| 4 | Crospovidone | 94.50 | 7.00 |
| 5 | Lactose monohydrate | 389.25 | 28.83 |
| 6 | Colloidal silicon dioxide | 6.75 | 0.50 |
| 7 | Magnesium stearate | 13.50 | 1.00 |
| Core Weight | | 1350 | |
| Coating weight buildup | | 27 | |
| Total tablet weight | | 1377 | |

Method of manufacture: The method of manufacturing process is same as that described in Example.5. The tablets are coated using the same composition as the coating composition of Example.5.

Example 7

600 mg Tablet Formulation

| S. No | Ingredients | Mg/tab | % w/w |
|---|---|---|---|
| 1 | Efavirenz (form-H1, $D_{90}$ = 5-10 microns) | 600.0 | 44.44 |
| 2 | Microcrystalline cellulose | 200.00 | 14.81 |
| 3 | Sodium lauryl sulfate | 46.00 | 3.41 |
| 4 | Crospovidone | 94.50 | 7.00 |
| 5 | Lactose monohydrate | 389.25 | 28.83 |
| 6 | Colloidal silicon dioxide | 6.75 | 0.50 |
| 7 | Magnesium stearate | 13.50 | 1.00 |
| Core Weight | | 1350 | |
| Coating weight buildup | | 27 | |
| Total tablet weight | | 1377 | |

Method of manufacture: The method of manufacturing process is same as that described in Example.5. The tablets are coated using the same composition as the coating composition of Example.5.

Example 8

200 mg Capsule Formulation

| S. No | Ingredients | Mg/Capsule | % w/w |
|---|---|---|---|
| 1 | Efavirenz (Form H 1) | 200.00 | 44.44 |
| 2 | Microcrystalline cellulose | 89.00 | 19.78 |
| 3 | Sodium lauryl sulfate | 15.33 | 3.41 |
| 4 | Crospovidone | 33.67 | 7.48 |
| 5 | Lactose monohydrate | 96.33 | 21.41 |
| 6 | Colloidal silicon dioxide | 9.00 | 2.00 |
| 7 | Magnesium stearate | 6.67 | 1.48 |
| Total weight | | 450 | |

Method of manufacture: The method of manufacturing process is same as that described in Example.1. The Lubricated blend is filled into capsules.

Example 9

Efavirenz, Emtricitabine and Tenfovir Disproxil Fumarate Combination

| Efavirenz Granulation | | | |
|---|---|---|---|
| S. No | Ingredients | Mg/tab | % w/w |
| 1 | Efavirenz (Form H 1) | 600 | 35.55 |
| 2 | Microcrystalline cellulose | 267 | 15.82 |
| 3 | Sodium lauryl sulfate | 46 | 2.73 |
| 4 | Croscarmellose sodium | 77 | 4.56 |
| 6 | Colloidal silicon dioxide | 27 | 1.60 |
| 7 | Magnesium Stearate | 20 | 1.19 |
| Emitricitabine and Tenofovir disproxil fumarate Compaction | | | |
| 8 | Emitricitabine | 200 | 11.85 |
| 9 | Tenofovir disproxil fumarate | 300 | 17.78 |
| 10 | Croscarmellose sodium | 38.5 | 2.28 |
| 11 | Microcrystalline cellulose | 89.5 | 5.30 |
| 12 | Colloidal silicon dioxide | 5 | 0.30 |
| 13 | Magnesium stearate | 17.68 | 1.05 |
| Core Weight | | 1350 | |
| Coating weight buildup | | 27 | |
| Total tablet weight | | 1377 | |
| Coating Material Composition | | | |
| 1 | Polyvinyl alcohol | | |
| 2 | Polyethylene glycol | | |
| 3 | Iron oxide red | | |
| 4 | Titanium dioxide | | |
| 5 | Talc | | |
| 6 | Black iron oxide | | |

Method of manufacture: Efavirenz is mixed with other ingredients and then wet granulated using an aqueous solution of sodium lauryl sulfate. This wet mass may then be dried in a fluid bed, tray or other suitable dryer. The dried granules are blended and lubricated. Emitricitabine and tenofovir disproxil fumarate is compacted with other excipients and lubricated. Emitricitabine, tenofovir disproxil fumarate final blend and efavirenz final blend are lubricated together with magnesium stearate and colloidal silicon dioxide and mixed together. This blend is compressed into tablets. The compressed tablets are film coated using the coating composition mentioned in example 9.

Dissolution Study:

The dissolution profile of the resulting coated tablets as per Example 6 and 7 were studied in 1000 ml of water with 2.0% sodium lauryl sulphate using USP-II apparatus at 50 rpm. The sampling was carried out at 10, 15, 20, 30, 45 minutes. The results are depicted in the table below:

| Time point (minutes) | % of drug release (Example 6) | % of drug release (Example 7) |
|---|---|---|
| 10 | 64 | 78 |
| 15 | 77 | 89 |
| 20 | 84 | 94 |
| 30 | 88 | 96 |
| 45 | 90 | 97 |

Bioequivalence Study:

Two products are considered to be bioequivalent if the 90% confidence interval (CI) of the relative mean $C_{max}$, $AUC_{(0-t)}$ and $AUC_{(0-\infty)}$ of the test to reference should be within 80.00% to 125.00% in the fasting state.

A two-way crossover bioequivalence study was carried out using the tablets of composition of Example 6 and 7. The study was monitored in terms of the AUC and $C_{max}$ achieved for efavirenz with the test and reference products. When study was conducted with the tablets made with efavirenz of particle size 100 microns, the 90% confidence intervals for the ratios of the log transformed mean values for $C_{max}$ and AUC for the test and reference product (T/R ratio) were outside the bioequivalence criteria. But when tablets made with particle size of 5-10 microns, 90% confidence intervals for the ratios of the log transformed mean values for $C_{max}$ and AUC for the test and reference product (T/R ratio) were with in the bioequivalence acceptance criteria.

From the bioequivalence studies conducted for pharmaceutical formulation of novel form of efavirenz, it has been observed that there is a requirement of special particle size to prepare a bioequivalent pharmaceutical formulation of novel polymorph of efavirenz and it can be achieved only by the process developed by the inventor.

We claim:

1. A process for preparing crystalline efavirenz form H1 particles, comprising wet milling an aqueous dispersion of 1 to 15% W/V crystalline efavirenz form H1 to water in a high speed homogenizer at a speed of 10000 to 30000 rpm and producing crystalline efavirenz form H1 particles wherein 90 volume-percent of the particles are in the range of 2 to 100 μm.

2. The process according to claim 1, wherein the aqueous dispersion further comprises a solvent selected from isopropanol, methanol, acetone, and mixtures thereof.

3. The process according to claim 1, wherein the concentration of the aqueous dispersion is 1.5 to 10% W/V crystalline efavirenz form H1 to water.

4. The process according to claim 3, wherein the aqueous dispersion comprises 5 to 8% W/V crystalline efavirenz form H1 to water.

5. The process according to claim 3, wherein the aqueous dispersion comprises 2 to 3% W/V crystalline efavirenz form H1 to water.

6. The process according to claim 1, where in the speed of homogenizer is 12000 to 28000 rpm.

7. The process according to claim 6, where in the speed of homogenizer is 15000 to 25000 rpm.

8. The process according to claim 1, wherein 90 volume-percent of the particles are in the range of 3 to 50 μm.

9. The process according to claim 8, wherein 90 volume-percent of the particles are in the range of 5 to 15 μm.

* * * * *